United States Patent

Cros et al.

[11] Patent Number: 5,989,831
[45] Date of Patent: Nov. 23, 1999

[54] HAPTEN ASSAY BY A COMPETITION-BASED METHOD

[75] Inventors: Philippe Cros; Nicole Battail, both of Lyons; Nadia Piga, Ecully, all of France

[73] Assignee: Bio Merieux, Marcy-l'Etoile, France

[21] Appl. No.: 08/860,298

[22] PCT Filed: Dec. 21, 1995

[86] PCT No.: PCT/FR95/01709

§ 371 Date: Jul. 8, 1997

§ 102(e) Date: Jul. 8, 1997

[87] PCT Pub. No.: WO96/19729

PCT Pub. Date: Jun. 27, 1996

[30] Foreign Application Priority Data

Dec. 21, 1994 [FR] France .................................. 94 15418

[51] Int. Cl.⁶ ........................ G01N 33/53; G01N 33/532
[52] U.S. Cl. ................... 435/7.1; 435/7.6; 435/7.93; 435/7.94; 435/7.95; 435/544; 436/544
[58] Field of Search ...................... 435/7.1, 6, 7.93–7.95; 436/544

[56] References Cited

U.S. PATENT DOCUMENTS

| 4,824,941 | 4/1989 | Gordon et al. | |
| 4,921,788 | 5/1990 | Deutsch | 435/6 |
| 5,223,393 | 6/1993 | Khanna et al. | 435/6 |
| 5,429,952 | 7/1995 | Garner et al. | 436/518 |
| 5,648,213 | 7/1997 | Reddy et al. | 435/6 |
| 5,656,731 | 8/1997 | Urdea et al. | 435/7.1 X |
| 5,849,480 | 12/1998 | Cros et al. | 435/6 |

FOREIGN PATENT DOCUMENTS

| A 0 620 439 | 10/1994 | European Pat. Off. . |
| WO-A 91-19812 | 12/1991 | WIPO . |
| WO-A 93-20074 | 10/1993 | WIPO . |
| WO-A 93-20094 | 10/1993 | WIPO . |

Primary Examiner—James C. Housel
Assistant Examiner—S. Devl
Attorney, Agent, or Firm—Oliff & Berridge, PLC

[57] ABSTRACT

Method of assaying hapten in a sample, in which said sample is placed in contact with antibodies capable of recognizing hapten and with a predetermined quantity of a reagent capable of competing with said hapten-fixing antibodies. The reagent is a conjugate formed by a single-stranded fragment of nucleic acid with a compound capable of being recognized by said hapten-recognizing antibodies. The fixed or unfixed reactant is detected by antibodies capable of recognizing the nucleic acid fragment of said conjugate. Detection of said reactant by anti-fragment antibodies of said nucleic acid enhances, in particular, the sensitivity of the assay.

5 Claims, 2 Drawing Sheets

HAPTEN ASSAY BY A COMPETITION-BASED METHOD

BACKGROUND OF THE INVENTION

1. Field of Invention

The present invention relates to a reagent for assaying haptens and its application.

Haptens are nonimmunogenic molecules, namely when they are alone they are incapable alone of triggering an immune reaction by antibody production, but are capable of being recognized by antibodies obtained by immunizing animals under known conditions, particularly by immunization with a hapten-protein conjugate.

2. Description of Related Art

Various techniques have been proposed for assaying haptens in a sample, including the so-called competition techniques. These techniques, described for the first time by Yalow and Berson (Nature, 184, p. 1648, 1959) for radioimmunoassay of plasma insulin, were applied to assaying haptens in the early 70s (Gharig H. et al. J. Clin. Endocrinol. Metab., 31, pp. 709–714, 1970; Abraham G. E., Acta Endocrinologica, suppl. 183, pp. 1–42, 1974).

According to these techniques, the hapten to be assayed is placed in competition, for binding to a given quantity of specific antibodies of said hapten, with a known, added quantity of the same, labeled, hapten. After a separation stage in which the free hapten (i.e. not linked to the antibodies) and the antibody-hapten complexes are separated, the quantity of labeled hapten, linked or free, is determined by the activity of the label. This measurement allows one to deduce the quantity of unlabeled hapten present at the outset. In this type of competition assay, the quantity of labeled hapten-antibody complex formed decreases as the quantity of unlabeled hapten is increased in the reaction medium.

According to a first embodiment of this type of competition assay, the hapten to be assayed and the labeled hapten react simultaneously with a predetermined quantity of specific antibodies of the hapten. After equilibrium, the free haptens are separated from the haptens bound to the antibodies. According to another embodiment, the reagents are added sequentially: in the first phase, the hapten to be assayed is added to a predetermined quantity of antibodies such that all the hapten to be assayed is bound. In the second phase, the labeled hapten is added in excess to saturate the antibody sites that have remained free and, after a sufficient incubation time, the unbound labeled hapten is separated.

Various methods for labeling haptens have been proposed. Radioactive labeling, although it offers the advantage of being sufficiently sensitive, has various drawbacks such as the instability of the label and the need for cumbersome equipment, and personnel protection and waste disposal measures, which are substantial constraints, particularly as far as automating the hapten assay test is concerned. Another option is to use an enzyme such as horseradish peroxidase, alkaline phosphatase, or beta-galactosidase as the label. Addition of the specific substrate of the enzyme reveals the quantity of free hapten or hapten bound to the antibody (Van Weemen B. K. and Schuurs A. H. W. M., FEBS Letters, 24(1), pp. 77–81, 1972 or Wisdom G. B., Clin. Chem., 22(8), pp. 1243–1255, 1976). This type of labeling has several advantages such as cost, ease of use, speed of enzyme reaction, absence of specific protective measures, and ability to automate the test.

It is known to specialists however that competition methods using an enzyme-labeled hapten are sometimes insensitive and may in some cases give results with low significance.

SUMMARY OF INVENTION

The present invention relates to a reagent for assaying haptens by a competition technique that palliates the aforesaid drawbacks.

More specifically, the invention relates to a method for assaying a hapten in a sample wherein: (a) said sample is placed in contact with a predetermined quantity of antibodies capable of recognizing said hapten and with a predetermined quantity of a reagent able to enter into competition with said hapten to bind to said antibodies by forming an antigen-antibody type complex, said reagent being a conjugate formed by a fragment of single-stranded nucleic acid with a compound capable of being recognized by the antibodies recognizing the hapten, and (b) with the aid of a label capable of binding with said reagent, the quantity of said reagent bound to said antibodies or the quantity of said reagent not bound to said antibodies is determined, said label being an antibody capable of recognizing said nucleic acid fragment. The quantity of hapten present in the sample is then deduced.

In particular embodiments, the quantity of bound or unbound reagent is determined by measuring the quantity of label bound to said reagent; for this purpose, the label capable of binding with said reagent is added and the quantity of bound or unbound reagent is determined by measuring the quantity of label bound either to the reagent bound to the antihapten antibodies or to the free, unbound reagent; said label is an antibody capable of recognizing said nucleic acid fragment of the conjugate; this antibody can itself be bound in known fashion to a tracing agent with a view to detection; this antibody can also be detected in known fashion by an anti-antibody itself bound to a tracing agent.

The method of the invention can be implemented by having the sample and the reagent simultaneously contact the antibodies capable of recognizing the hapten; for example, in this case, the sample and the reagent can be mixed before they contact the antibodies.

The method of the invention can also be implemented sequentially. In this case, in the first phase, the sample can be placed in contact with the antibodies capable of recognizing the hapten and in the second phase, the reagent can be added.

In the remainder of the specification, the term "compound" will be used to designate the constituent of the conjugate bound to the nucleic acid fragment. Said constituent is a compound recognized by the antibodies recognizing the hapten to be assayed. This compound can be either the hapten itself or an analog of this hapten.

In the present application, the term "hapten" designates compounds that generally have a molecular weight less than 3000 Da and usually less than 2000 Da, which can be for example peptides, glycosylated peptides, metabolites, vitamins, hormones, prostaglandins, toxins, or various drugs.

The hapten can be chosen for example from:

a glycosylated peptide such as the N-terminal sequence of the beta subunit of human hemoglobin;

thyroid hormones, particularly thyroxine, triiodothyronine, and tetraiodothyronine; steroidal hormones, particularly estrogens such as estriol and estradiol, androgens such as testosterone, progestogens such as progesterone, glucocorticoids such as 11-desoxycorticosterone and cortisol; catecholamines such as adrenaline, noradrenaline, and dopamine;

vitamins A, B such as B12, C, D, E, and K, folic acid, biotin, thiamin;

drugs such as digoxin, digitoxigenin, digitoxin, digoxigenin; antibiotics particularly aminoglycosides, gentamicin, tobramycin, amikacin, sisomicin, kanamycin, netilmicin, penicillin, tetracycline, tetramycin, chloromycetin, and actinomycetin; or phenobarbital, primidone, ethosuximide, carbamazepine, valproate, theophylline, caffeine, propanolol, procainamide, quinine, amitriptyline, desipramine, disopyramide, amphetamines, morphine, methadone, barbiturates;

nucleosides and nucleotides such as adenosine di- or triphosphate (ADP and ATP), flavine mononucleotide (FMN), nicotinamide adenine dinucleotide (NAD), its phosphate derivative (NADP), thymidine, guanosine, and adenosine;

toxins such as alphatoxin, cholera toxin, staphylococcus enterotoxin B, and the like.

In the present application, the term "antibody" includes polyclonal or monoclonal antibodies, antibodies obtained by genetic recombination, and antibody fragments such as Fab or F(ab')$_2$ fragments.

The antibodies capable of recognizing hapten are also called "anti-hapten antibodies" here.

The single-stranded nucleic acid fragment present in the conjugate is in particular chosen from the group consisting of a DNA fragment, an RNA fragment, a DNA/RNA hybrid fragment, or a fragment of modified RNA or DNA. In particular, a single-stranded fragment not capable of self-pairing can be used.

In general, the single-stranded nucleic acid fragment contains no more than 100 nucleotides, in particular no more than 40 nucleotides.

The nucleic acid fragment is for example an oligodeoxyribonucleotide or an oligoribonucleotide with 2 to 100 nucleotides, more particularly 10 to 40 nucleotides, or a deoxyribonucleotide or a ribonucleotide, or a deoxyribonucleoside or a ribonucleoside.

The nucleic acid fragment can be a modified nucleic acid fragment having for example one or more modified pairs or can be composed solely of natural modified bases (such as 6-ketopurine, xanthine, 5-methylcytosine, 2-aminopurine) or modified bases that are not natural (such as thioguanine or 8-oxoguanine). The nucleic acid fragment can be composed solely or partially of nucleosides modified on the oside part such as carbonucleosides, or may have modifications to the phosphodiester skeleton, for example phosphorothioate groups. It can also be composed totally or partially of nucleosides with alpha or beta anometry or D or L series isomers. A modified nucleic acid fragment contains at least one modification such as those listed above.

The reagent used in the process of the present application is a conjugate resulting from binding of a nucleic acid fragment with a compound which is either the hapten to be assayed or an analog of this hapten, said analog being capable of being recognized by antibodies recognizing the hapten to be assayed.

More specifically, the nucleic acid fragment and the compound comprised of the hapten or the hapten analog are bound by a covalent bond to form a composite molecule called "conjugate." For this purpose, known methods of establishing a covalent bond can be used. For example, when the nucleic acid fragment is prepared by automatic synthesis, the hapten can be added as a nucleotide during synthesis, in the 5' and/or 3' position, or in any other position in the nucleotide chain. This necessitates prior preparation of a derivative of the hapten usable in automatic synthesis, for example a phosphoramidite, H-phosphonate, or phosphotriester derivative, or preparation of a nucleotide substituted by said hapten on the purine or pyrimidine base, or on the oside part. Said hapten can also be introduced during synthesis on internucleotide phosphoruses by oxidative phosphoramidation. Regarding these methods, the survey by S. L. Beaucage and R. P. Iver, Tetrahedron 49, 1925–1963 (1993) for example may be cited.

Derivatives of the nucleic acid fragment and the hapten can also be prepared in order to introduce a reactive functional group to each, the groups introduced being capable of reacting with each other and forming a covalent bond. For example, a primary amino group carried by one of the derivatives will react with the N-hydroxysuccinamide ester of the other derivative which contains a carboxyl group; likewise, a thiol group will react with a maleimide, pyridylisulfide, or alkyl halide group and a phosphorothioate will react with an alkyl halide.

Reactive functional groups allowing binding via a coupling agent can also be introduced to the nucleic acid fragment and said compound (hapten or hapten analog).

The term "coupling agent" as used here designates a molecule containing at least two reactive groups of the same nature or different natures (homobifunctional or heterobifunctional coupling agent). For example, a primary amine group and a carboxylic acid group can form an amide bond in the presence of a coupling agent such as a carbodiamide, or two primary amino groups can be coupled in the presence of a coupling agent such as phenylene-1,4-diisothiocyanate or disuccinimidylsuberate.

The reactive groups introduced (or already present) in the nucleic acid fragment can be chosen for example from the amine, hydrazine, hydrazone, imide, amide (possibly substituted), semicarbazone, carbonyl (particularly an aldehyde group), sulfide, thiol, carbamate, nitrile, halogen, hydroxyl, sulfonamide, isocyanate, isothiocyanate, carboxylic acid, carboxylic acid ester, carboxylic acid halide, acid anhydride, epoxide, phosphate, phosphorothioate, phosphite, phosphonate, thiophosphate, etc. The reactive groups can be temporarily protected, particularly when oligonucleotides are synthesized.

The reactive groups that can be introduced (or are possibly present) on the other constituent of the conjugate (namely, on a compound which is either the hapten or a hapten analog) with a view to the reaction with a nucleic acid derivative can be chosen for example from the same groups as those listed above, it being understood that, to form the conjugate, a hapten derivative having a reactive group capable of reacting, as the case may be, either with the reactive group present on the nucleic acid fragment derivative or with a reactive group present on the coupling agent is chosen.

Introduction of these reactive groups to the nucleic acid fragments and hence grafting of said compound to the nucleotide fragment can be done in any position of the nucleotide chain using for example reagents synthesized by known methods or commercially available reagents. For example, the modifications can be made in the 5' position by using a reagent such as Aminolink II (Applied Biosystems, No. 400808), or in the 3' position by using a solid substrate such as that sold by Clontech Lab Inc. under No. 5221, or described by Reed et al. (1991) Bioconjugate Chem. 2, 217–225. These modifications can be made to the nucleic bases (Glen Research, No. 101039), or to the oside part by modifying the oside part and using for example a ribofuranose substituted in the 2' position in place of a deoxy-2'-ribofuranose (Yamana et al. (1991) Tetrahedron Lett. 32, 6347–6350), or substituting a nucleoside by an alkylamine residue (Clontech Lab. Inc., No. 5203), or by substituting an internucleotide phosphate using the protocols described by Froehler et al., (1988) Nucl. Acids Res., 16, 11, 4831–4839; Conway et McLaughlin (1991) Bioconjugate Chem., 2, 452–457; Letsinger et al. (1989) Proc. Natl. Acad. Sci. USA, 86, 6553–6556.

Likewise, if necessary, said compound (hapten or the like) can be modified by introducing a reactive group known of itself at any appropriate position on said compound. Methods of introducing reactive groups are furnished in particular in "Preparation of Antigenic Steroid-Protein Conjugate," F. Kohen et al., in Steroid Immunoassay, Proceedings of the Fifth Tenovus Workshop, Cardiff, April 1974, ed. E H D Cameron, S H. Hillier, K. Griffiths, as for example introducing a hemisuccinate group in the 6,11, 20, or 21 position, a chloroformiate group in the 11 position, or a carboxymethyl group in the 6 position, in the case of progesterone.

The antibody capable of recognizing the nucleic acid fragment of the conjugate can be for example a nucleic acid anti-fragment antibody, particularly a monoclonal antibody, as described by P. Cros et al. (Nucleic Acids Research, 22 (15), 2951–2957, 1994).

Said antibody can be bound to a tracer, particularly by covalence.

The tracer can in particular be chosen from:

enzymes that produce a detectable signal, for example by colorimetry, fluorescence, or luminescence, such as horseradish peroxidase, alkaline phosphatase, beta-galactosidase, or glucose-6-phosphate dehydrogenase;

chromophores such as fluorescent, luminescent, or staining compounds;

groups whose electron density is detectable by electron microscopy or by electrical properties such as conductivity, amperometry, voltametry, or impedance measurements;

groups detectable by optical methods such as diffraction, surface plasmon resonance, variation in contact angle, or physical methods such as atomic spectroscopy, or tunnel effect.

In another embodiment of the invention, the nucleic acid antifragment antibody is not bound to a tracer and, in this case, it is detected with an anti-antibody as indicated above, said anti-antibody being itself bound to a tracer.

The reactions involved in the method of the invention (complex formation with antibodies, possibly binding of labeling agents) are conducted under the usual conditions well known for this type of reaction in the presence of a liquid phase (generally a buffered aqueous solution) allowing the reagents to come in contact and react by formation of antigen-antibody type complexes, hybridization of complementary nucleic fragments, etc.

Depending on the method employed and the hapten to be assayed, adjustment of the experimental conditions, particularly determination of the quantity of antibody placed in contact with the sample and the quantity of conjugated reagent can be done ahead of time by methods well known to the individual skilled in the art to ensure better sensitivity and better reproducibility. For this purpose, a titration curve can first be plotted to determine the dilution of the antibody to be used in the assays. This dilution corresponds to an optical density value located in the linear part of the curve, for example an optical density value of between 50% and 75% of the value corresponding to the saturation threshold of the reading. Other information will be given in the experimental part below.

The quantity of conjugate bound to the antihapten antibody (or free, unbound conjugate) in the assay method of the invention can be evaluated by an appropriate detection method in a manner known of itself.

The detection reaction can involve for example:

a first step in which an antibody with a special affinity for the nucleic acid fragment of said conjugate is bound. This antibody can be revealed by using a tracer (for example, it is linked to the tracer). Or it can be revealed, in a manner known of itself, using another antibody capable of recognizing said anti-(nucleic acid fragment) antibody, said other antibody being itself bound to a tracer;

a second step, called development, whose nature is chosen according to the type of tracer used to label said detection agent. This tracer and its development method will in particular be chosen from those described above.

It is of course obvious that said first and second steps can be carried out separately or simultaneously in a manner known of itself.

Moreover, in the method of the invention, it is generally useful to accomplish a step in which the conjugate (and possibly the hapten) which has remained free and the conjugate (and possibly the hapten) bound to the antihapten antibody are separated to evaluate either the quantity of free conjugate or the quantity of conjugate bound to the antibodies.

Numerous well-known techniques can be used for this separation, particularly:

immunoprecipitation by a second antibody directed against the antihapten antibody can be effected, said second antibody being supplied either as a liquid or as a solid, for example being bound to inert particles;

one can use antibodies specific to the hapten to be assayed which have first been bound to a solid substrate, then the free conjugate can be eliminated merely by washing.

The antibody can be bound to the solid phase by various methods, either directly by passive adsorption or by covalent coupling, or indirectly using a second antibody or the streptavidin-biotin pair or the like. For example, streptavidin is bound to the solid phase and biotin is coupled to the hapten-specific antibodies.

The term "solid substrate" as used here includes all materials on which a biological molecule can be immobilized for use in diagnostic tests and separation processes. Natural or synthetic or chemically modified or unmodified materials can be used as the solid substrate, in particular polysaccharides such as cellulose-based materials, for example paper, cellulose derivatives such as cellulose acetate and nitrocellulose, dextran; polymers such as polyvinyl chlorides, polyethylenes, polystyrenes, polyacrylates, polyamides, or copolymers based on styrene-type monomers, unsaturated carboxylic acid esters, vinylidene chloride, dienes, or compounds with nitrile groups (such as acrylonitrile); vinyl chloride/propylene or vinyl chloride/acetate copolymers; natural fibers such as cotton and synthetic fibers such as nylon; inorganic materials such as silica, glass quartz, or ceramics; latexes, namely colloidal aqueous dispersions of any water-insoluble polymer; magnetic particles; metal derivatives, etc.

The solid substrate can in particular be in the form of a microtitration plate, a sheet, a cone, a tube, pellets, particles, or the like.

BRIEF DESCRIPTION OF DRAWINGS

In the attached drawings.

DETAILED DESCRIPTION OF PREFERRED EMBODIMENT

Figure 1:
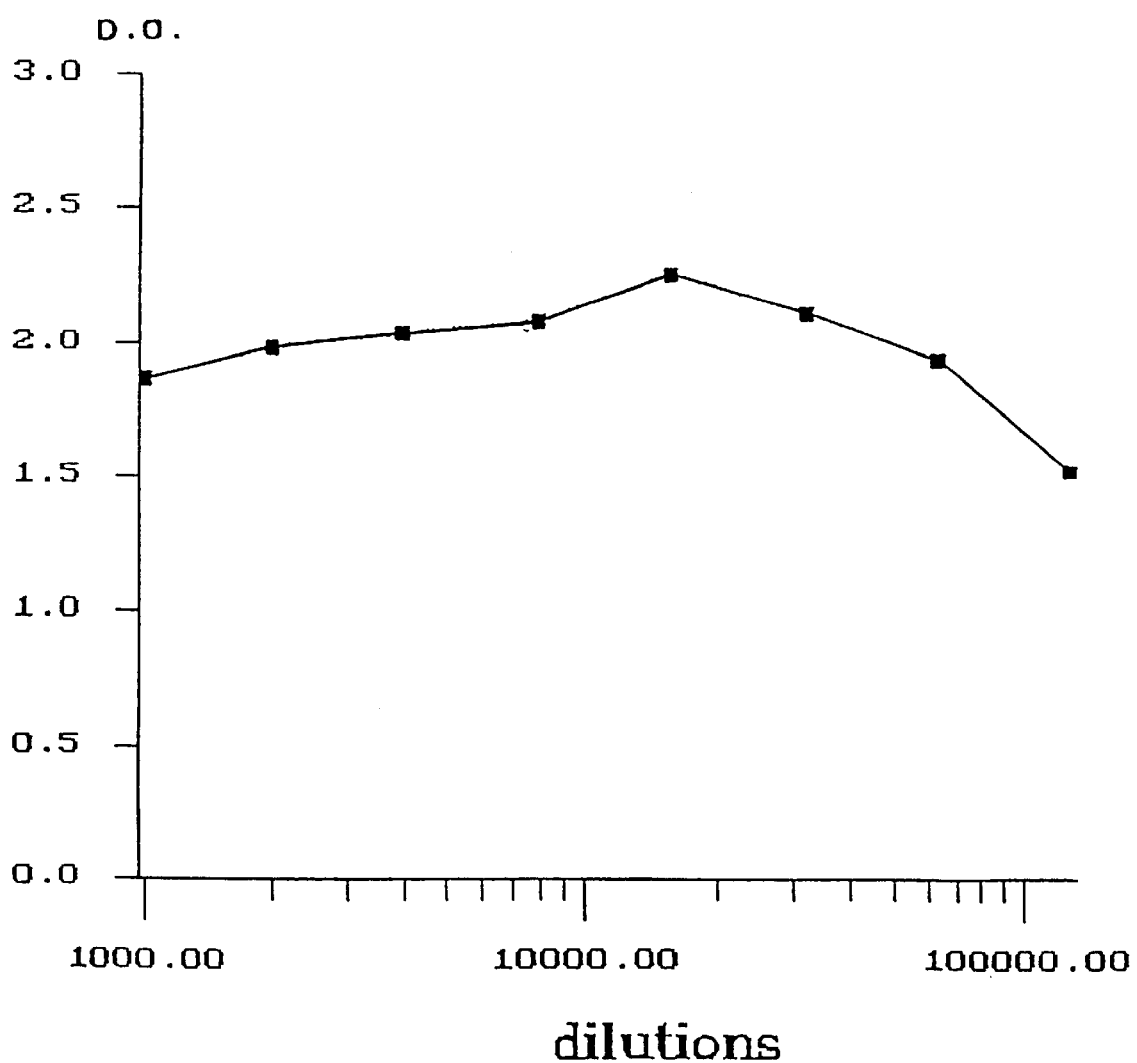
FIG. 1 shows the titration curve of the anti-estradiol monoclonal antibody obtained in Example 2(a) below with an alkaline phosphatase estradiol conjugate. Each point represents the mean of two experimental values minus the measurement value for nonspecific binding.

The following examples illustrate the invention.

EXAMPLE 1

Obtaining Oligonucleotide-Steroid Conjugates

Oligonuleotides are synthesized with the automatic unit 394 made by Applied Biosystems using phosphoramidite chemistry according to the manufacturer's protocol. To allow an oligonucleotide to be coupled to a hapten in a given position, reactive groups are introduced to the oligonucleotides by means of ligands compatible with automatic synthesis.

The phosphoramidite ligand (aminolink2, No. 400808 from Applied Biosystems) is added to the 5' end of the oligonucleotide according to the standard automatic synthesis protocol. Thus, the reactive group, used for grafting to a hapten, is located at the 5' end of the oligonucleotide.

After deprotection overnight at 55° C. in a 33% $NH_4OH$ solution and precipitation in the presence of ethanol at −20° C., the oligonucleotides are dried under vacuum and 1 mL of $H_2O$ is added.

The modified oligonucleotides are then purified by reverse-phase, high-pressure liquid chromatography (HPLC) on a Brownlee RP18 (10 mm/25 cm) column.
Conditions: flowrate 4.6 mL/min
  10% to 35% buffer B gradient in 30 min.
  35% to 100% buffer B gradient in 3 min.
with
  buffer B: 50% buffer A+50% $CH_3CN$ and
  buffer A: triethylammonium acetate (TEAA) 0.1 M; pH=7.00

The oligonucleotides modified by the aminolink2 arm and used in the present invention are described in Table 1.

TABLE 1

| Usual Oligonucleotide Number | SEQ ID No. | Nucleotide | Tr |
|---|---|---|---|
| 57 | 1 | beta | 19.54 |
| 196 | 2 | alpha | 23.21 |

The beta nucleotides are natural nucleotides, namely the glycoside link is in the beta anomeric form, contrary to the alpha nucleotides in which the glycoside link is in the alpha anomeric form. The oligonucleotides containing the alpha nucleotides were prepared according to the article by F. Morvan et al., Nucleic Acid Research, 16(3), pages 833–847, 1988.

Tr represents the retention time in minutes of the oligonucleotide under the following conditions:
Brownlee column RP18 (4.6 mm–25 cm)
Conditions: flowrate 1 mL/min
  10% to 35% buffer B gradient in 30 min.
  35% to 100% buffer B gradient in 3 min Coupling of Modified Oligonucleotide Synthesized on a Hapten The hapten derivatives used are described in Table 2.

TABLE 2

| Hapten Under Assay | Hapten Derivative Used for Coupling | Supplier |
|---|---|---|
| ESTRADIOL | ESTRADIOL-6-CARBOXYMETHOXIME-N-HYDROXYSUCCINIMIDE ESTER | BOEHRINGER MANNHEIM |
| TESTOSTERONE | TESTOSTERONE-19-HEMISUCCINATE-N-HYDROXYSUCCINIMIDE ESTER | BIO MERIEUX |

The testosterone derivative supplied by Bio Mérieux is prepared by the method described in J. Steroid Biochem., 23(6a), pp. 981–989, 1985, by A. White et al.

The oligonucleotide (50 nmoles) is dried in the rotary evaporator and treated with 20 μL of 0.1 M sodium borate buffer with pH 9.3. 300 μL of a hapten derivative solution (5 mg/mL in DMF) is added dropwise and the mixture obtained is agitated for 3 hours at 50° C. After centrifugation, the supernatant is separated and the centrifugation residue is added to 100 μL of water. The supernatant reserved is then added and 250 μL of 3 M ammonium acetate pH 5.2 and 5 mL chilled absolute ethanol (−20° C.) are added to the mixture obtained. After 30 min. incubation at −80° C. and centrifugation, the residue is added to 500 μL of water.

The oligonucleotide-hapten conjugate obtained is purified by HPLC under the following conditions:
Beckman ODS column (10 mm/25 cm)
Conditions: flowrate 4.6 mL/min
  20% to 30% buffer B gradient in 10 min.
  30% to 70% buffer B gradient in 20 min The conjugate collected is dried in the rotary evaporator then added to 500 μL of water.

Analogously, different oligonucleotide-hapten conjugates were prepared. The nature of the conjugates obtained is summarized in Table 3.

TABLE 3

| Oligonucleotide-Hapten Conjugate | Oligonucleotide | Hapten | Tr |
|---|---|---|---|
| A | 57 | ESTRADIOL | 16.18 |
| B | 196 | ESTRADIOL | 15.65 |
| C | 57 | TESTOSTERONE | 27.96[a] |

In Table 3, Tr is the retention time of the product purified under the following conditions:
Brownlee column RP 300 (4.6 mm/100 mm)
Conditions: flowrate 1.0 mL/min
  20% to 30% buffer B gradient in 10 min.
  30% to 70% buffer B gradient in 20 min
(a) for conjugate C, the gradient is 10 to 40% of B in 30 min.

EXAMPLE 2

Estradiol Assay by Competition (a) According to the Prior Art (i) An anti-estradiol monoclonal antibody obtained by the technique described by G. Köhler and C. Milstein (Nature 256, 495–497 (1975)) is obtained after immunizing BALB-c mice with a bovine estradiol-albumin conjugate (this conjugate is obtained by reacting the estradiol derivative of Table 2 with albumin) and used at a concentration preestablished by plotting a titration curve.

The titration curve is obtained as follows: in the wells of a Maxisorb NUNC polystyrene microtitration plate (sold by Polylabo Paul Block, No. 4-39454), 100 μL per well of a 5 μg/mL solution of anti-(IgG (H+L) mouse) goat antibody (sold by Jackson Immuno Research Laboratories, No. 115-005-062) is deposited in a bicarbonate buffer (0.05 M NaHCO$_3$; pH 9.6). This plate is incubated overnight at 22° C. or 1 hour at 37° C. The plate is washed 3 times in 300 μL of 0.05% PBS TWEEN® buffer (0.15 M NaCl; 0.05 M sodium phosphate; pH 7.0; TWEEN® 20 at a final concentration of 0.05% (TWEEN®: trade name). The locations in the plate not occupied by the antibody are saturated by adding 100 μL of a PBS milk solution, 1% final concentration (0.15 M NaCl; 0.05 M sodium phosphate; pH 7.0; Régilait skim milk (trade name) 1%). It is incubated for 1 hour at 37° C. then rinsed 3 times with 300 μL of 0.05% PBS TWEEN® buffer. In each well of the plate, 100 μL of successive dilutions of the anti-estradiol antibody in PBS buffer are added. After incubation for 1 hour at 37° C., the plate is rinsed 3 times with 0.05% PBS TWEEN® buffer. To each well, 50 μL of human male serum (sold by Bio Mérieux, No. 66581) and 50 μL of estradiol-alkaline phosphatase conjugate are added (the estradiol is conjugated with alkaline phosphatase by formation of an N-hydroxysuccinimide ester and coupling with dicyclohexylcarbodiimide as described by Mattox et al., J. Steroid Biochem., 10, pp. 167–172, 1979). It is allowed to incubate for 1 hour at 37° C.

The plate is rinsed 3 times with 0.05% PBS TWEEN® buffer then once with distilled water. 100 μL of PNPP substrate (paranitrophenyl phosphate sold by Sigma under No. 104-0) at the concentration of 2 mg/mL in diethanolamine HCl buffer (diethanolamine 1.29 M; MgSO$_4$ 0.56 mm, NaNO$_3$ 38 mm; 0.012 N HCl; pH 9.8) are added to each well. After incubation for 30 minutes at 37° C., the enzyme reaction is blocked by adding 100 μL of 1 N NaOH. The reading is done at 405 nm on a Biowhittaker Microplate Reader 2001. The titration curve obtained is shown in FIG. 1.

This titration curve allows one to determine the dilution of the anti-estradiol antibody that will be eventually used and which corresponds for example to an OD of 1.5–2 at 405 nm.

(ii) The estradiol molecule is assayed under competition conditions by a similar protocol but in this case, addition of the estradiol-alkaline phosphatase conjugate is replaced by addition of 50 μL of a solution chosen from solutions of increasing estradiol concentration diluted in human male serum containing no haptens (Bio Mérieux, No. 66581), and 50 μL of estradiol-alkaline phosphatase conjugate prepared as described above. This preparation is incubated for 1 hour at 37° C.

The measurements are made after a development step in the presence of the enzyme substrate as described above. The results are presented in Table 4.

TABLE 4

| Estradiol Concentration pg/mL | O.D. 405 nm (*) |
|---|---|
| 0 | 1.755 |
| 10 | 1.749 |
| 100 | 1.646 |
| 1000 | 1.194 |
| 10,000 | 0.289 |
| 100,000 | 0.078 |

(*) Each result represents the mean OD of two experiments minus the nonspecific binding value (reading 405 nm).

The results of the calibration range presented in Table 4 shows that inhibition of binding of the estradiol-alkaline phosphatase conjugate is obtained when the estradiol concentration increases. The value representing 50% fixation inhibition of the estradiol-alkaline phosphatase conjugate corresponds to a concentration of 2200 pg/mL of estradiol.

(b) Utilization of an Oligonucleotide-Estradiol Conjugate Developed by a Labeled Anti-Oligonucleotide Antibody Unless stated to the contrary, the equipment and reagents used are the same as previously.

Figure 2:
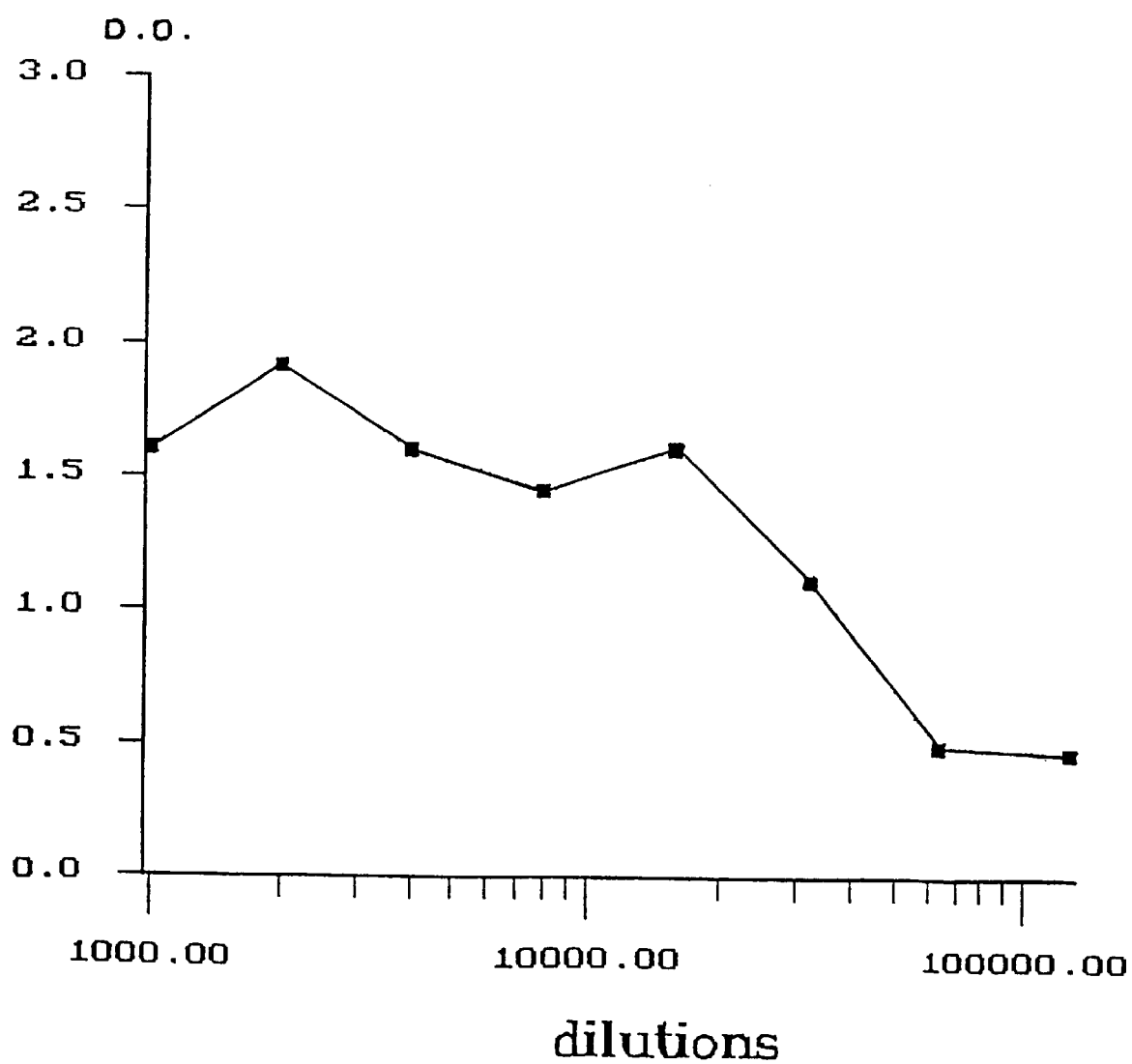
FIG. 2 represents the titration curve of the anti-estradiol monoclonal antibody obtained in Example 2(b) below with an estradiol-oligonucleotide conjugate (estradiol-oligonucleotide 196 obtained in Example 1). Each point represents the mean of two experimental values minus the measurement value for nonspecific binding.

(i) The titration curve is obtained as follows: in the wells of a microtitration plate, at the rate of 100 μL per well, a 1 μg/mL solution of an anti(IgG (H+L) mouse) goat antibody in a bicarbonate buffer (0.05 M NaHCO$_3$; pH 9.6) is deposited. It is left to incubate overnight at 22° C. or 1 hour at a temperature of 37° C. The plate is washed 3 times with 300 μL of 0.05% PBS TWEEN® buffer (0.15 M NaCl; 0.05 M sodium phosphate; pH 7.0; TWEEN® 20 at a final concentration of 0.05% (TWEEN®: trade name)). The locations on the plate not occupied by the antibody are saturated by adding 100 μL of a PBS milk solution with a 1% final concentration (0.15 M NaCl; 0.05 M sodium phosphate; pH 7.0; Régilait skim milk (trade name) 1%). After incubation for 1 hour at 37° C., it is rinsed 3 times in 300 μL of PBS TWEEN® 0.05% buffer. To each well of the plate, 100 μL of different successive dilutions of the anti-estradiol antibody solution in PBS buffer are added and left to incubate for 1 hour at 37° C. The plate is rinsed 3 times with 0.05% PBS TWEEN® buffer then the sites not occupied by the anti-estradiol antibody are saturated by adding 100 μL of a PBS-(0.15 M NaCl; 0.05 M sodium phosphate; pH 7.0) solution containing 10% of murine ascites fluid produced from the T-180 sarcoma cell line (sold by Bio Mérieux under No. 30202). This preparation is left to incubate for 1 hour at 37° C. then rinsed 3 times in 300 μL of 0.05% PBS TWEEN® buffer. 50 μL of human male serum are added to each plate well and mixed with 50 μL of conjugate B (see Example 1) in 0.72 nM solution in the PBS. The preparation is incubated for 1 hour at 37° C. then washed 3 times in 300 μL of 0.05% PBS TWEEN® buffer. Also, the anti-oligonucleotide monoclonal antibody described by P. Cros et al. (article cited above) was purified from ascites fluid by ABx ion exchange chromatography (Backer 726900) then conjugated with alkaline phosphatase (Boehringer) by the technique of S. Avrameas (Immunochem., 6. p. 43, 1969). A solution of this antibody diluted to 1:400 (total protein concentration 1 mg/mL) in PBS buffer—1% human male serum—1% normal goat serum—10% murine ascites fluid (from the T-180 sarcoma cell line) is prepared. 100 μL of this antibody solution is added to the wells in the plate. After incubation for 1 hour at 37° C. and rinsing 3 times with 0.05% PBS TWEEN® buffer then rinsing with distilled water, 100 μL of PNPP substrate at a concentration of 2 mg/mL in diethanolamine HCl buffer (1.29 M diethanolamine; MgSO$_4$ 0.56 mm, NaNO$_3$ 38 mm; 0.012 N HCl; pH 9.8) are added to the plate wells. The preparation is incubated for 30 minutes at 37° C. then the reaction is stopped by adding 100 μL of 1 N NaOH. The plates are read at 405 nm on a Biowhittaker Microplate Reader 2001. The titration curve obtained is shown in FIG. 2. This titration curve allows the dilution of the anti-estradiol antibody that will be used, corresponding for example to an OD of 1–1.5 at 405 nm, to be determined.

(ii) The estradiol compound is then assayed under competition conditions the same protocol as in stage (i) above, but in this case 50 μL of a solution chosen from increasing estradiol concentration solutions, diluted in hapten-free human serum (Bio Mérieux No. 66581), are added to 50 μL of the 0.75 nM solution of conjugate B, then left to incubate for 1 hour at 37° C.

The remainder of the experiment is done as described above. The results are presented in Table 5:

TABLE 5

| Estradiol Concentration pg/mL | O.D. 405 nm (*) |
|---|---|
| 0 | 1.551 |
| 10 | 1.277 |
| 100 | 1.210 |

TABLE 5-continued

| Estradiol Concentration pg/mL | O.D. 405 nm (*) |
|---|---|
| 1000 | 0.731 |
| 10,000 | 0.190 |
| 100,000 | 0.130 |

(*) Each result represents the mean OD of two values minus the nonspecific binding value (reading 405 nm).

These assay results with the competition technique show that inhibition of complex binding (conjugate B/anti-oligonucleotide-alkaline phosphatase antibody) is achieved when the estradiol concentration increases. The value representing 50% inhibition of the binding of this complex corresponds to a concentration of 900 pg/mL of estradiol.

Analogously, using an anti-testosterone antibody, conjugate C (see Example 1) and, for labeling, antibodies directed against oligonucleotide 57 (see Example 1), the sensitivity of the testosterone assay is improved relative to assays according to the prior art conducted similarly to that described in Example 2(a).

What is claimed is:

1. A method for determining the presence or amount of a hapten in a sample, said method comprising:
   (a) contacting said sample with (i) a predetermined quantity of antibody which specifically binds said hapten and (ii) a predetermined quantity of a competitor of said hapten, wherein said competitor is a conjugate of a single-stranded nucleic acid fragment and said hapten or an immunological analog thereof;
   (b) separating the bound from the unbound competitor;
   (c) contacting either the bound or the unbound competitor with a detection reagent comprising a detectably labelled antibody which specifically binds to said nucleic acid fragment; and
   (d) measuring the amount of the bound or the unbound detectably labelled antibody in order to determine the presence or amount of said hapten in said sample.

2. The method of claim 1, wherein said nucleic acid fragment contains a maximum of 100 nucleotides.

3. The method of claim 1, wherein said nucleic acid fragment contains a maximum of 40 nucleotides.

4. The method of claim 1, wherein the competitor is contacted with the sample before the sample is placed into contact with the antibodies.

5. The method of claim 1, wherein the competitor is contacted with the sample after the sample is placed into contact with the antibodies.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: SYNTHESIZED OLIGONUCLEOTIDE 57

(ix) FEATURE:
      (D) OTHER INFORMATION: /note= "ALKYLAMINE ARM (AMINOLINK2)
         AT 5' END"

(xi) SEQUENCE DESCRIPTION: SEQ ID NO:1:

ACTAAAAACT AGTAATGCAA AG      22

(2) INFORMATION FOR SEQ ID NO:2:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: SYNTHESIZED OLIGONUCLEOTIDE 196

(ix) FEATURE:
            (D) OTHER INFORMATION: /note= "ALPHA ANOMERIC NUCLEOSIDES
                AND ALKYLAMINE ARM (AMINOLINK2) AT 5' END"

(xi) SEQUENCE DESCRIPTION: SEQ ID NO:2:

ACCCCGAGAT TTACGTTATG T                                              21

(2) INFORMATION FOR SEQ ID NO:3:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: SYNTHESIZED OLIGONUCLEOTIDE 2466

(ix) FEATURE:
            (D) OTHER INFORMATION: /note= "ALKYLAMINE ARM (AMINOLINK2)
                AT 5' END"

(xi) SEQUENCE DESCRIPTION: SEQ ID NO:3:

CTTTGCATTA CTAGTTTTTA GT                                             22